United States Patent [19]
Adams et al.

[11] Patent Number: 5,458,620
[45] Date of Patent: Oct. 17, 1995

[54] CARDIAC ARRHYTHMIA DETECTION USING INTERDEPENDENT MULTIPLE PARAMETER SETTINGS

[75] Inventors: Theodore P. Adams, Edina; Mark W. Kroll, Minnetonka, both of Minn.

[73] Assignee: Angeion Corporation, Plymouth, Minn.

[21] Appl. No.: 195,557

[22] Filed: Feb. 14, 1994

Related U.S. Application Data

[63] Continuation-in-part of Ser. No. 837,952, Feb. 20, 1992, Pat. No. 5,312,443.

[51] Int. Cl.⁶ ..................................................... A61N 1/39
[52] U.S. Cl. ............................................ 607/5; 128/705
[58] Field of Search .................................... 607/5, 18, 19; 128/705

[56] References Cited

U.S. PATENT DOCUMENTS 5,312,443  5/1994  Adams et al. .......................... 607/5

*Primary Examiner*—Lee S. Cohen
*Assistant Examiner*—Jeffrey R. Jastrzab
*Attorney, Agent, or Firm*—Patterson & Keough

[57] ABSTRACT

A programmable implantable cardioverter defibrillator (ICD) provides signals from a plurality of cardiac sensing modalities to a control circuit within the ICD that analyzes the signals and determines whether to deliver an electrical countershock therapy. An interdependent detection parameter threshold is programmably established for each of a programmably selectable combination of two or more cardiac sensing modalities by selecting at least two corner points that will define a boundary condition for a given cardiac dysrhythmia. Whenever the threshold is exceeded, the control circuit automatically diagnoses a cardiac dysrhythmia and delivers a preprogrammed electrical countershock therapy regimen for the diagnosed dysrhythmia. Multiple interdependent detection parameter thresholds may be combined in a variety of ways. More than one combination of two or more cardiac sensing modalities may be used to define a multivariant boundary condition for the given cardiac dysrhythmia. Alternatively, more than one set of corner points for a particular combination of cardiac sensing modalities may be used so as to create multiple detection envelopes, one for each different type of cardiac dysrhythmia. Finally, both of these options may be programmed together so as to allow for the definition of multivariant performance envelopes for different cardiac dysrhythmias.

10 Claims, 5 Drawing Sheets

CARDIAC ARRHYTHMIA DETECTION USING INTERDEPENDENT MULTIPLE PARAMETER SETTINGS

CROSS REFERENCE TO CO-PENDING APPLICATIONS

The present invention is a continuation-in-part of U.S. patent application Ser. No. 07/837,952 entitled IMPROVED ARRHYTHMIA-DETECTION CRITERIA PROCESS FOR A CARDIOVERTER/DEFIBRILLATOR filed Feb. 20, 1992 and assigned to the same assignee as the present invention now U.S. Pat. No. 5,312,443. The present invention is also related to a application, U.S. patent application Ser. No. 08/125,288 entitled OVERCHARGED FINAL COUNTERSHOCK FOR AN IMPLANTABLE CARDIOVERTER DEFIBRILLATOR filed Sep. 22, 1993 and to U.S. patent application Ser. No. 08/033,632 entitled IMPLANTABLE CARDIOVERTER DEFIBRILLATOR HAVING A SMALLER DISPLACEMENT VOLUME filed Mar. 15, 1993 now abandoned, which are incorporated herein by reference and assigned to the same assignee as the present invention.

FIELD OF THE INVENTION

This invention relates generally to the field of cardiac cardioversion and defibrillation and more specifically to implantable cardioverter defibrillators (ICD) and the multiple detection parameters to diagnose and treat cardiac dysrhythmias.

BACKGROUND OF THE INVENTION

Despite substantial progress over the last several decades, heart disease and its associated dysrhythmias remains one of the most prevalent causes of death in the world. In-hospital experience utilizing continuous cardiac monitoring revealed that prompt detection and diagnosis of cardiac dysrhythmias allows for rapid treatment and reversal of the cardiac dysrhythmia. Diligent physician and nursing intervention interrupts the natural progression of the patient's disease and increases the survival rate. This in-hospital experience is predicated upon trained personnel being able to recognize and correctly diagnose a patient's cardiac dysrhythmia and then provide the appropriate treatment.

Recent years have shown substantial progress in the development of automatic implantable cardioverter defibrillator systems or ICD's. These electronic standby cardioverter defibrillators will, in response to detection of abnormal cardiac rhythms, countershock the heart muscle via implanted electrodes with sufficient energy to depolarize the heart and mass. This countershock technique is directed at abolishing the origins of the pathologic dysrhythmia, thereby allowing the natural pacing activity of the heart to reestablish its dominance restoring the normal cardiac rhythm.

In general, several electronic standby defibrillator systems are disclosed in the prior art with examples such as U.S. Pat. Nos. 3,614,954 and 3,614,955. Other efforts in the field have resulted in the disclosure of implantable electrodes for use by automatic electronic cardioverter defibrillators, for example U.S. Pat. No. 4,030,509 issued to Hellman et al.

The one salient feature of all implantable cardiac devices is the necessity to detect electrical activity of the heart and form a diagnosis based on that detection. Typically, the first step in the detection process is to sense the electrocardiogram, amplify that signal, pass it through low pass and high pass filters, and from the resultant peaks generate a digitized signal representative of the electrocardiographic tracing. It is readily apparent that this digitized signal is easily detected, counted and measured for purposes of diagnostic paradigms in determining the presence or absence of cardiac arrhythmias. It then follows that the cardiac rate provides a simple threshold upon which to make a diagnosis of cardiac arrhythmia. If a preset heart rate threshold is surpassed, the diagnosis of cardiac arrhythmia is made and the appropriate treatment is carried out by the automatic ICD. Numerous systems incorporate heart rate as a detection parameter and incorporate the results of the detection within the diagnostic paradigms.

Simple straight forward application of a heart rate determination must be modified, however, in order to avoid an inadvertent defibrillation countershock in a person who may have sustained a rate of 250 beats per minute for a few beats. Such a patient may have simply sustained a premature ventricular contraction, or PVC. PVCs are abnormal contractions arriving soon after a normal ventricular contraction such that the interval measurement may equal or exceed the set heart rate threshold being monitored by the system. PVCs may not be benign by nature, but treatment for PVCs with electrical countershock therapy is inappropriate. The most common and simplest method of modification has been to additionally incorporate a duration parameter within the diagnostic paradigms such that an abnormally high heart rate must be sustained for a given number of beats before the automatic system will diagnose a cardiac arrhythmia and proceed with a countershock. Referring to FIG. 2, the X axis can be duration of tachycardia interval and the Y axis can be beats per minute. Thresholds are programmed within the system's diagnostic paradigm which derives a single point determination denoted here as X,Y such that if exceeded in both X and Y, as noted by the hash mark area, then a diagnosis of cardiac arrhythmia is made and treatment is carried out.

Other systems utilize different means of detection and threshold parameters. U.S. Pat. Nos. 4,184,493 and 4,202,340 both issued to Langer, disclose a system using a probability density function (PDF) to determine the presence or absence of ventricular fibrillation. Langer's system is such that a single point threshold is programmed and if the characteristic measured by the PDF is detected beyond the single point threshold, then a diagnosis of ventricular fibrillation will be made and countershock treatment would be carried out. Langer's system also disclosed a cardiac impedance measurement which was connected in a logical AND to the probability density function. If both events occur simultaneously, a single point threshold is reached and ventricular fibrillation would be diagnosed and countershock treatment carried out. While different than the traditional detection techniques, this system still fits the general characteristics of the graph in FIG. 2 where the X axis could be represented by the probability density function threshold and the Y axis could be presence of high or low impedance within the myocardium. As shown in FIG. 2, the single point (X,Y) is a logical AND connection of the X parameter and the Y parameter such that when both are satisfied then the determination falls within the hash mark area resulting in a diagnosis of fibrillation and subsequent treatment.

U.S. Pat. No. 4,475,551 issued to Langer, et al., again returns to the use of a probability density function approach to the detection of ventricular fibrillation. Langer recognized that the probability density function alone was insensitive and required modification. Langer coupled his probability density function in a logical AND with the heart rate, defining single thresholds for both. Again utilizing FIG. 2, this approach still defines a single point (X,Y) threshold determination beyond which satisfies the logical AND requirement. The end result continues to use the determination of a single point as a logical combination threshold that is either exceeded or rot.

There have been a number of patents describing various monitoring parameters. Examining these prior art disclosures reveal that almost all fall within the concept depicted in FIG. 2 such that one parameter can be placed on the abscissa, the second parameter on the ordinate, and single point thresholds satisfying the defined relationships are created. These thresholds are linked by a logical AND function whereby if both thresholds are exceeded, the point will fall within the hash mark area, diagnosis of cardiac arrhythmia is made and treatment is carried out.

U.S. Pat. No. 3,805,795 issued to Denniston and Davis discloses a system where the parameters monitored are myocardial contraction and heart rate. U.S. Pat. No. 4,796,620 issued to Imran discloses a system utilizing high cardiac contraction rate acceleration coupled with absence of a subsequent cardiac contraction rate deceleration linked in a logical AND to a high heart rate threshold. Imran attempts to avoid difficulties of confusing exercise induced tachycardia from pathologically induced ventricular tachycardia. U.S. Pat. No. 4,865,036 issued to Chirife disclosed two sets of parameters. The first set compared heart rate and a pre-ejection period. The second set of parameters in Chirife's disclosure measured the heart rate increase set against an absolute heart rate. U.S. Pat. No. 4,880,005 issued to Pless and Sweene disclosed a system which set four programmable detection criteria: high heart rate; rate stability; sudden onset; and sustained high rate. On the surface this may seem as a departure from the previous prior art disclosures but further analysis of Pless and Sweene's disclosure reveals that once again only single point thresholds are set for each of these four criteria and compared in a one-by-one fashion connected by logical ANDs. Other detection parameters have been mentioned within the prior art such as monitoring blood flow, pH, $pCO_2$, $pO_2$, arterial blood pressures, and body temperature. In all circumstances, a single point value threshold is set for each parameter. Through coupling by a logical AND to other parameters, a single point logical combinational threshold is set that is either exceeded or not.

The above mentioned detection systems have been developed in an effort to better delineate between the various ventricular arrhythmias. All of these attempts have been hobbled, however, because they are always limited to providing a single point threshold, ignoring the reality that none of these physiologic conditions relate to one another in such a fashion.

At the opposite end of the complexity scale are the neural networks with representative cases being the parent case of the present invention, U.S. patent application Ser. No. 07/837,952 entitled ARRHYTHMIA-DETECTION CRITERIA PERMITTING VARIATIONS IN INDIVIDUAL CARDIAC VARIABLES now U.S. Pat. No. 5,312,443 and U.S. Pat. No. 5,251,626 issued to Nickoils et al. entitled APPARATUS AND METHOD FOR THE DETECTION AND TREATMENT OF ARRHYTHMIAS USING A NEURAL NETWORK. In general, these detection systems disclose the use of neural networks or the use of complex mathematical functions to perform the detection and diagnosis for an ICD. While these type of systems have the potential for greater accuracy in detection and diagnosis of cardiac dysrhythmias, the problem is that neural networks and complex mathematical functions are overly complicated and difficult to program or train. In the case such as an ICD, where a neural network must make decisions that will ultimately determine whether a patient might live or die, such a device cannot afford the luxury of learning by its mistakes as is done to train most types of neural networks. Therefore, in order to teach a neural network sufficient information to perform its detection and diagnostic function effectively, the neural network must be derived prior to implantation of the device, something which is a difficult and time consuming process if customized to each individual patient.

Unfortunately, it is difficult to derive a neural network for effective detection and diagnosis that would be common to many patients because of the wide differences in patient conditions and needs. For example, the complexity required to program or train these systems effectively precludes an attending physician from altering the diagnostic parameters in response to information learned during the implantation procedure. Finally, the complexity of these types of diagnostic techniques necessarily increases the complexity and power consumption of the ICD which can lead to a potential increase in device failures as well as a decrease in device life span.

Any given patient with heart disease is at risk to develop a cardiac arrhythmia. In order to successfully treat the occurrence of an arrhythmia, an automatic implantable cardioverter defibrillator must contain within it the ability to distinguish accurately and consistently among the various ventricular tachycardias and provide the appropriate countershock technique to reverse the detected cardiac arrhythmia. Furthermore, any diagnostic paradigm must not only be able to distinguish among the various abnormal pathologic ventricular tachycardias but also distinguish the detected tachycardia from benign forms of ventricular tachycardia which do not require electrical intervention. Development of diagnostic paradigms to carry out this task have led to the development of the numerous above-mentioned parameters utilized by these detection systems in attempts to carry out appropriate delineation between the various tachycardias encountered. As noted, almost all of these systems choose a single programmable threshold level for each parameter and then connect it in a logical AND combination to a second parameter resulting in a single point logical combinational threshold, as universally depicted in FIG. 2. Only if both parameters are exceeded simultaneously can the system be confident it has detected an abnormal ventricular tachycardia and proceed with treatment.

The presence of so many diagnostic parameters merely indicates the severe limitation the single point logical combinational threshold paradigm places on existing diagnostic systems. While some of these diagnostic systems have recognized the limit of using only a single combinational threshold, these references teach that the way to overcome this limitation is to add more single point logical combinational thresholds on top of each other. Unfortunately, even these improved diagnostic systems still continue to have difficulty in reaching an appropriate diagnosis.

At the other end of the spectrum, other diagnostic systems have proposed the use of a complicated mathematical functions or neural network to interrelate a variety of cardiac detection parameters. While these systems may theoretically provide for a more accurate diagnosis, these systems are complicated to implement and also to program. What is needed is an improved programmable parameter system and method for more accurate interpretation and diagnosis of abnormal and benign ventricular tachycardias.

SUMMARY OF THE INVENTION

The present invention is a method and apparatus for the automatic detection and treatment of cardiac dysrhythmias by a programmable implantable cardioverter defibrillator (ICD). The ICD provides signals from a plurality of cardiac sensing modalities to a control circuit within the ICD that analyzes the signals and determines whether an electrical countershock therapy should be delivered through a plurality of implantable electrodes placed about the heart. An interdependent detection parameter threshold is established for each of a programmably selectable combination of two or more cardiac sensing modalities by selecting at least two corner point values that will define a boundary condition for the particular combination of cardiac sensing modalities for a given cardiac dysrhythmia. Whenever the threshold is exceeded by the signals for the selected combination of cardiac sensing modalities, the control circuit automatically diagnoses a cardiac dysrhythmia and delivers a preprogrammed electrical countershock therapy regimen for the diagnosed dysrhythmia. Multiple interdependent detection parameter thresholds may be combined in a variety of ways. More than one combination of two or more cardiac sensing modalities may be used to define a multivariant boundary condition for the given cardiac dysrhythmia. Alternatively, more than one set of corner points for a particular combination of cardiac sensing modalities may be used so as to create multiple detection envelopes, one for each different type of cardiac dysrhythmia. Finally, both of these options may be programmed together so as to allow for the definition of multivariant detection envelopes for different cardiac dysrhythmias.

The invention provides for ease of use by an attending physician during implantation and programming of the ICD by allowing as few as two corner points to be chosen for each chosen combination of cardiac sensing modalities in order to define each interdependent detection parameter threshold. This allows for relatively simple programming of the ICD, but retains the flexibility to customize the ICD to the specific needs of a particular patient. The invention also allows for a number of detection envelopes to be defined, one for each different type of cardiac dysrhythmia which the attending physician determines should be treated by the ICD. Typically, these different types of cardiac dysrhythmias might include ventricular fibrillation, high rate ventricular tachycardia and low rate ventricular tachycardia, although other cardiac dysrhythmias could also be diagnosed and treated by the ICD. Each of these dysrhythmias will include its own individual therapy regimen which may also be customized by the attending physician based on an understanding of the needs of the particular patient.

In contrast to most prior art diagnostic techniques, the boundary condition of an interdependent detection parameter threshold of the present invention for a particular combination of cardiac sensing modalities for a given cardiac dysrhythmia is always defined by more than one logical combination point. Implementation and programming of the interdependent detection parameter threshold, however, does not require the complexity of a neural network or mathematical function in order to increase the effectiveness and flexibility of the detection and diagnostic function of an automatic ICD.

DETAILED DESCRIPTION OF THE INVENTION

Figure 1:
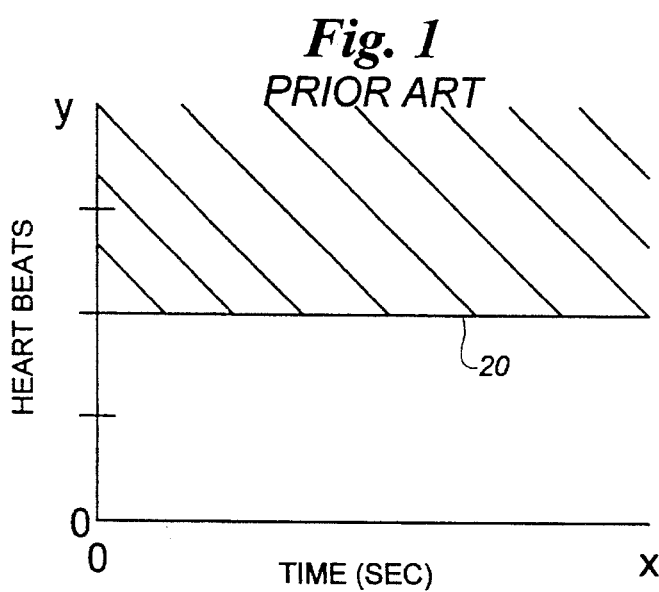
FIG. 1 is a graphic representation of a prior art use of number of heart beats over time to determine detection of a dysrhythmia.

The purpose of defining more accurately the true nature of ventricular arrhythmias, also described as dysrhythmias, has become important because treatment for the various arrhythmias should be approached differently. In general, heart rates always considered acceptable and not requiring electrical treatment are in a range of below about 120 beats per minute. Above this rate an implantable cardioverter defibrillator (ICD) must be able to discriminate between a normal tachycardia that is exercise or stress induced versus the various pathologic or abnormal ventricular tachycardias and ventricular fibrillation.

The pathological dysrhythmia known as ventricular tachycardia can be clinically subdivided into two subclasses. The first can be described as the low rate, or slow ventricular tachycardia usually in the range of approximately 120 to about 180 beats per minute. The single most important feature of slow ventricular tachycardia is the presence of a perfusing pulse. These patients are not in immediate danger of dying soon after the onset of the low rate ventricular tachycardia.

Contrast this low rate ventricular tachycardia with high rate, or fast ventricular tachycardia which generally is in the approximately 180 to about 250 beat per minute range. Here the single most important characteristic is that patients suffering from this arrhythmia have a significantly diminished or absent perfusion pulse. Depending upon the severity of the hypotension, these patients are in imminent danger of death within the next several minutes. Often, a fast rate ventricular tachycardia deteriorates to ventricular fibrillation, adding to the sinister outlook for ventricular tachycardia and heightening the need for urgent treatment.

Ventricular fibrillation is characterized as a very rapid and chaotic ventricular rate. Under these conditions, no perfusion pulse is generated, the ventricles being most aptly described as appearing like a ball of quivering writhing worms. These patients collapse within seconds of the onset of the ventricular fibrillation and, if there is no timely intervention to reverse the arrhythmia, brain death ensues within several minutes.

The general approach in using ICD's has been to treat ventricular fibrillation with defibrillation electrical countershocks in the range of 25 to 40 joules generated by high voltage capacitors charged to approximately 600 to 750 volts. In the event that an initial countershock is unsuccessful in terminating the ventricular fibrillation, a typical treatment regimen will increase the discharge voltage and repeat the countershock up to five times.

High rate ventricular tachycardia, despite its severity and grim prognosis, is treated differently from ventricular fibrillation. High rate ventricular tachycardia has been known to deteriorate to ventricular fibrillation when given an asynchronous defibrillation countershock. Therefore, because high rate ventricular tachycardia is still organized and synchronous electrically, a desirable treatment approach to high rate ventricular tachycardia is to first attempt a synchronized cardioversion of electrical countershock approximately 1 to 5 joules. If this is unsuccessful, treatment is increased to a higher energy level, usually starting in the range of 5 to 25 joules, but is still synchronized with the detected high rate ventricular tachycardia. If the high rate ventricular tachycardia proves to be resistent after several cardioversion attempts, only then should the system utilize a high energy asynchronous defibrillation mode.

Low rate ventricular tachycardia is also highly synchronized and by definition is able to generate a perfusing pulse. The important caveat is to avoid subjecting the patient to an electrical cardioversion treatment that will convert them from an abnormal but life sustaining arrhythmia to an abnormal terminal arrhythmia. Like high rate ventricular tachycardia, the low rate can also be inadvertently converted to a high rate tachycardia or fibrillation with the inappropriate use of electrical therapeutic intervention. Therefore, the usual approach for low rate ventricular tachycardia is to attempt bursts of overdrive pacing, defined as pacing the heart at a rate greater than the tachycardia. This technique utilizes pacemaker level energies of approximately 10 to 50 microjoules per pulse for a burst duration of approximately 10 pulses per burst. If the first burst is unsuccessful and the patient remains in a low rate ventricular tachycardia, subsequent bursts are reattempted.

For low rate tachycardia, no attempts are made to automatically increase the countershocks to cardioversion or defibrillation levels of countershocks unless the patient's condition deteriorates after an overdrive pacing burst. The reasoning behind such a "failure mode" approach is predicated on the fact that cardioversion countershocks and defibrillation countershocks have a higher incidence of inadvertently causing low rate ventricular tachycardias to deteriorate to dangerous high rate ventricular tachycardia and even ventricular fibrillation. This would place the patient in imminent danger of death where they might not have been with just the overdrive pacing bursts. Therefore, in attempts to avoid inadvertent deterioration of a circumstance that is not yet life threatening, automatic cardioverter defibrillator systems should not subject a patient to the higher energy countershocks while still diagnosed as being in a low ventricular tachycardia.

For a more complete description of treatments for the various ventricular arrhythmias, reference is made to the previously identified U.S. patent application Ser. No. 08/125,288 entitled OVERCHARGED FINAL COUNTERSHOCK FOR AN IMPLANTABLE CARDIOVERTER DEFIBRILLATOR.

Ventricular fibrillation, high rate and low rate ventricular tachycardias must all be delineated from other tachycardia arrhythmias because these other rhythms rarely require electro-stimulation as a first line treatment. These other tachycardia rhythms are generally found in three categories: those arising from physical stress and exercise; rapid ventricular response to atrial fibrillation; and supraventricular tachycardia. Of course, exercise and stress induced tachycardia is best treated by removing the stress or cessation of exercise. Atrial fibrillation induced rapid ventricular response and supraventricular tachycardia generally do not require cardioversion and can be successfully treated chemically. Even if requiring electrocardioversion, the determination when to use countershock therapy for atrial fibrillation and supraventricular tachycardia is best made by a physician in attendance. Systems that incorporate atrial fibrillation therapy as an automatic treatment mode are commendable for patients where it has been proven that their atrial fibrillation leads to excessively rapid ventricular rates. In these patients, the high ventricular rates exceed their cardiac reserves and drastically decrease the diastolic filling times causing loss of perfusion pressure and lowered cardiac output detrimental to the patient. Certainly, still other patients do not tolerate chemical conversion and therefore electrical cardioversion would become their primary choice of treatment. Electrical cardioversion methods for an implanted system to treat atrial fibrillation and supraventricular tachycardia employ low energy in the range less than 1 joule delivered as a synchronized countershock to the atria.

Representative sensing modalities are heart rate, beat to beat interval, interval instability, duration of sustained ventricular dysrhythmia, and acceleration of heart rates. Such a representative list is by no means exhaustive of all sensing modalities available.

Figure 11:
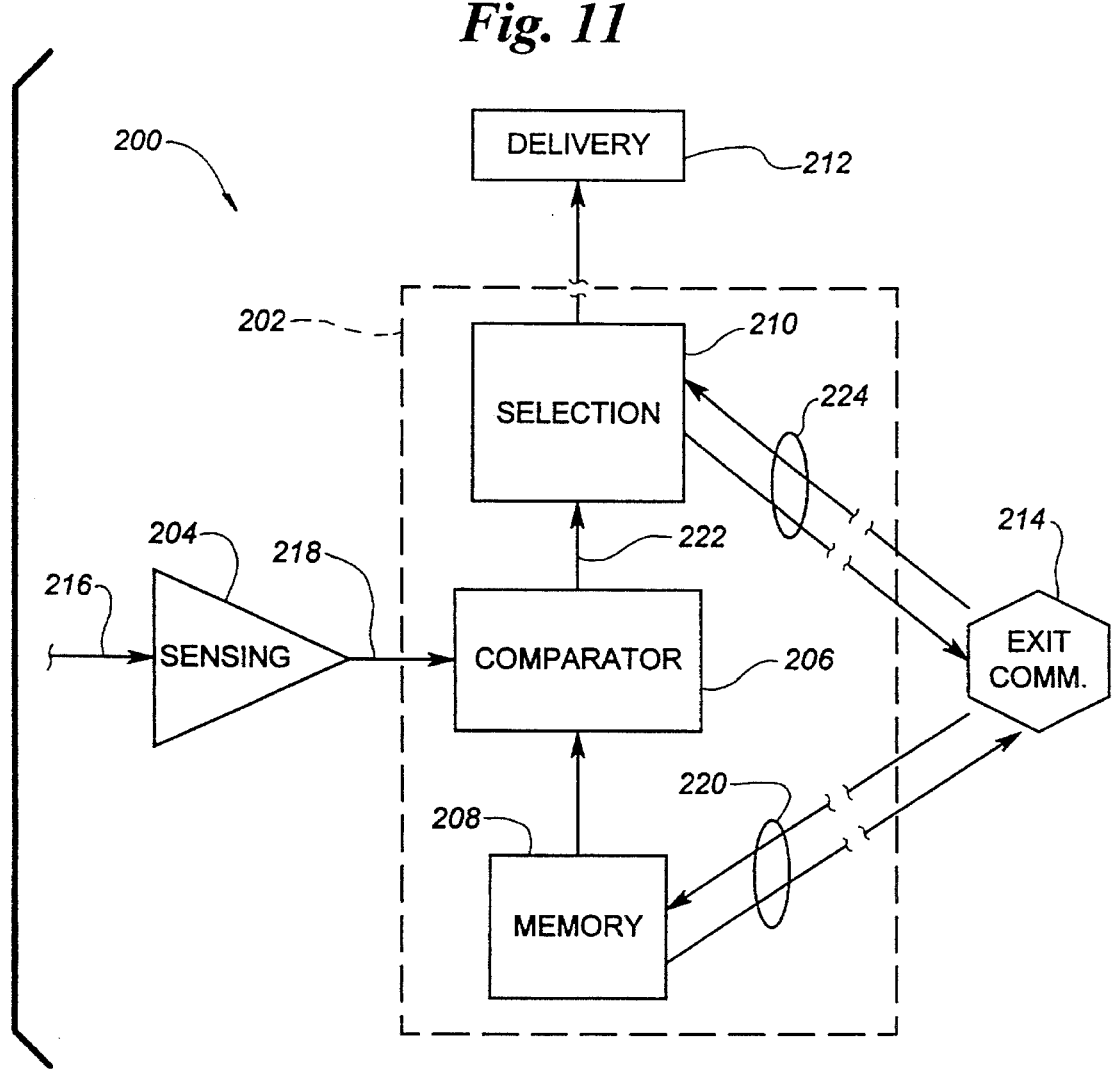
FIG. 11 is a block diagram of a preferred embodiment of the present invention.

Referring now to FIG. 11, a block diagram of an ICD in accordance with the present invention will be described. For a more detailed description of the circuitry and mechanics of the preferred embodiment of an ICD in accordance with the present invention, reference is made to the previously identified U.S. patent application Ser. No. 08/033,632 entitled IMPLANTABLE CARDIOVERTER DEFIBRILLATOR HAVING A SMALLER DISPLACEMENT VOLUME. It will be recognized that the present invention is equally applicable to any automatic ICD system having control circuitry, such as logic circuitry or a microprocessor and control software or a combination of both, that is capable of receiving signals representative of a plurality of cardiac sensing modalities and, in response, performing the disclosed detection and diagnostic techniques. Representative cardiac sensing modalities would include heart rate, beat to beat interval, interval instability, duration of sustained ventricular dysrhythmia and acceleration of heart rate. Signals which are representative of cardiac sensing modalities based on sensed physical parameters other than electrocardiogram data may also be used. These examples of cardiac sensing modalities are representative of the types of sensed signals which could be utilized with the present invention and it is intended that other kinds of sensed signals are included within the scope of the present invention.

FIG. 11 is a block diagram of an operational flow chart in a detection system 200 comprising a control means 202 and a sensing means 204 for providing electrical signals representative of a plurality of cardiac sensing modalities. Control means 202 includes a comparator means 206, memory means 208, and selection means 210. System 200 also includes a countershock delivery means 212 and an external communications interface 214.

As shown in FIG. 11 sensing means 204 monitors via sensing input 216 a plurality of cardiac sensing modalities and provides electrical signals representative of those sensing modalities to comparator 206 via line 218. Memory means 208 stores values received via communication pathway 220 from interface 214 for defining one or more interdependent detection parameter thresholds. Comparator means 206 compares the electrical signals from sensing means 204 with the values stored in memory means 208 to arrive at a diagnosis of the presence or absence of a cardiac dysrhythmia. The result from comparator means 206 is sent to selecting means 210 via line 222 for selecting one or more of the preprogrammed electrical countershock therapies to be delivered by delivery means 212. Selecting means 210 receives programming from interface 214 via communication pathway 224. Pathways 220 and 224 are bi-directional allowing for interrogation of control means 202 to determine which modalities are being monitored, which interdependent detection parameter thresholds have been set, the number and types of dysrhythmia diagnoses performed and the subsequent treatment carried out for each diagnosis.

Figure 3:
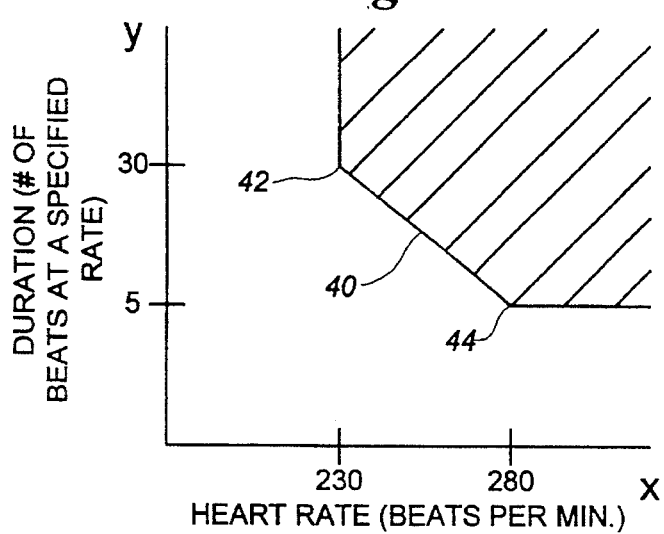
FIG. 3 is a graphic representation of an interdependent detection parameter threshold for the combination of duration and heart rate detected as defined by two corner points.

Referring to FIG. 3 there is depicted a graphic representation of curve 40 as a boundary condition comparing the duration as number of beats sustained at a specified rate versus heart rate at beats per minute to define a detection envelope. Points 42 and 44 on curve 40 represent two corner points chosen by a physician operator of the invention. Corner points 42 and 44 are chosen independently by the physician operator and in the particular example given, corner point 42 has been chosen to represent an interdependent detection parameter threshold as a duration of 30 and a heart rate of 230 and where corner point 44 is an interdependent detection parameter threshold as a duration of 5 and a heart rate of 280. Other number combinations can be chosen by the physician relying on the physician's best judgment in ascertaining the particular patient's needs. In operation, any combination of detected values falling within the hash mark area would be identified by an implantable cardioverter defibrillator using the present invention as a dysrhythmia and appropriate treatment will then be administered.

Figure 4:
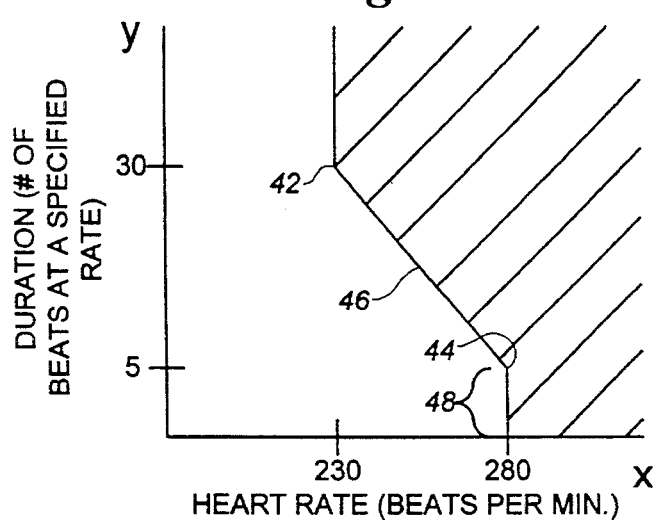
FIG. 4 is a graphic representation of an interdependent detection parameter threshold for the combination of duration and heart rate detected further defining a rate ruling zone.

FIG. 4 is a graphic representation of the present invention disclosing boundary condition curve 46, a curve similar to curve 40 in FIG. 3 in that for purposes of simplicity and clarification the same two corner points 42 and 44 have been chosen by a physician operator and input into the present invention as interdependent detection parameter thresholds. FIG. 4 further discloses curved segment 48 at the 280 beat per minute rate. This added hash mark area is identified as a rate ruling zone since the area to the right of 280 beats per minute is included into the hash mark area and would result in the present invention returning a confirmation of a treatable dysrhythmia. The significance of this rate ruling zone is that it is independent of duration. The rate ruling zone adds a further dimension to the concept behind the present invention increasing the versatility of the present invention whereby the invention is able to recognize that any heart rate beyond 280 beats per minute will be presumed a ventricular dysrhythmia amenable to electrical countershock treatment regardless of the duration of that dysrhythmia. In the preferred embodiment, the rate ruling zone concept is programmable as a separate alternative parameter to the points chosen to describe the performance envelope.

Figure 5:
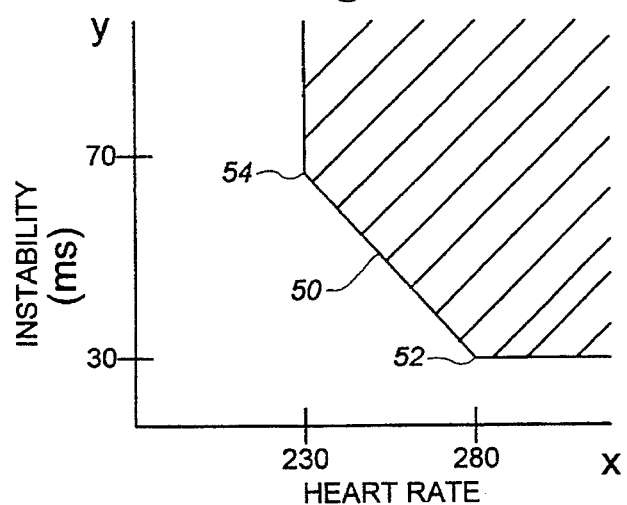
FIG. 5 is a graphic representation of an interdependent detection parameter threshold for the combination of instability and heart rate detected.

FIG. 5 is a graphic representation of the relationship of rhythm instability to heart rate. As used in the present invention, rhythm instability is calculated by taking the standard deviation in milliseconds of the beat intervals. A utility in using an instability parameter is to better define the ventricular dysrhythmia being detected. A low rate ventricular tachycardia is characteristically a very stable dysrhythmia compared with, for example, a highly unstable ventricular fibrillation. A high rate ventricular tachycardia characteristically has a stability level somewhere between low rate ventricular tachycardia and ventricular fibrillation. In FIG. 5, boundary condition curve 50 is defined by plotting corner points 52 and 54 defining a detection envelope such that a ventricular dysrhythmia is diagnosed if the ventricular characteristics detected fall within the hash mark area. Corner points 52 and 54 are chosen independently by the physician operator and in the particular example given, corner point 52 has been chosen to represent an interdependent detection parameter threshold as an instability of 30 msec and a heart rate of 280 and where corner point 54 is an interdependent detection parameter threshold as an instability of 70 msec and a heart rate of 230. Other number combinations can be chosen by the physician relying on the physician's best judgment in ascertaining the particular patient's needs. Curve 50 in FIG. 5 has been defined to select for ventricular fibrillation. Corner point 52 also defines a lower limit boundary recognizing that instability less than 30 milliseconds regardless of rate cannot be ventricular fibrillation since this level of stability is not typically associated with ventricular fibrillation.

Figure 6:
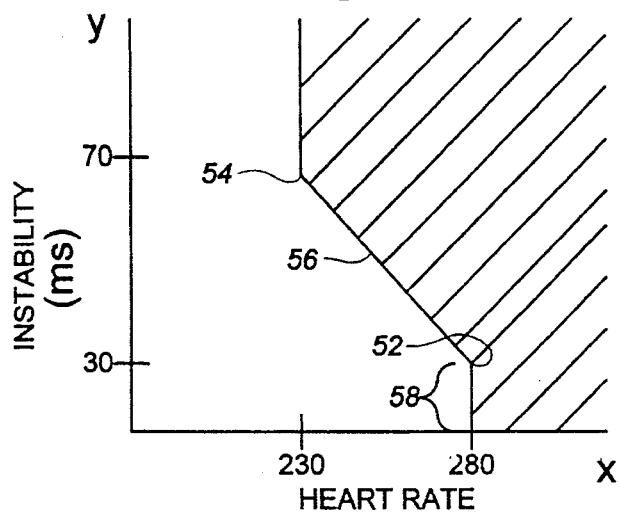
FIG. 6 is a graphic representation of an interdependent detection parameter threshold for the combination of instability and heart rate detected further defining a rate ruling zone.

FIG. 6 is a graphic representation of a similar boundary condition curve 56 to that of curve 50 in FIG. 5. As in FIG. 5, corner points 52 and 54 have been chosen for use in FIG. 6 as a representative example of the criteria limit parameters for defining ventricular fibrillation. An advantage of the present invention is the rate ruling zone 58 whereby a physician may decide that any rate greater than 280 beats per minute regardless of stability and despite ventricular fibrillation being characteristically unstable, that such a high rate warrants treatment.

Figure 7:
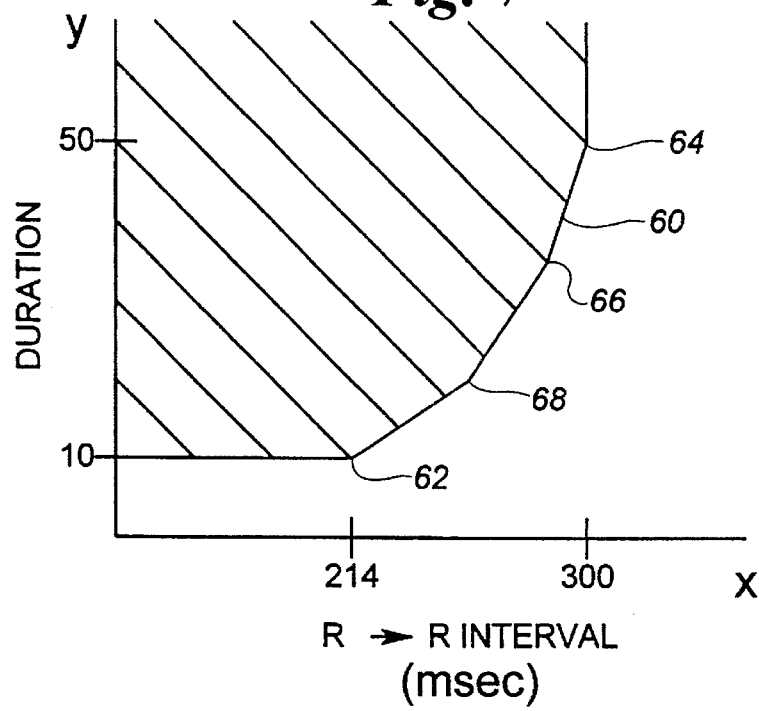
FIG. 7 is a graphic representation of an interdependent detection parameter threshold for the combination of instability and a R to R interval.
Figure 8:
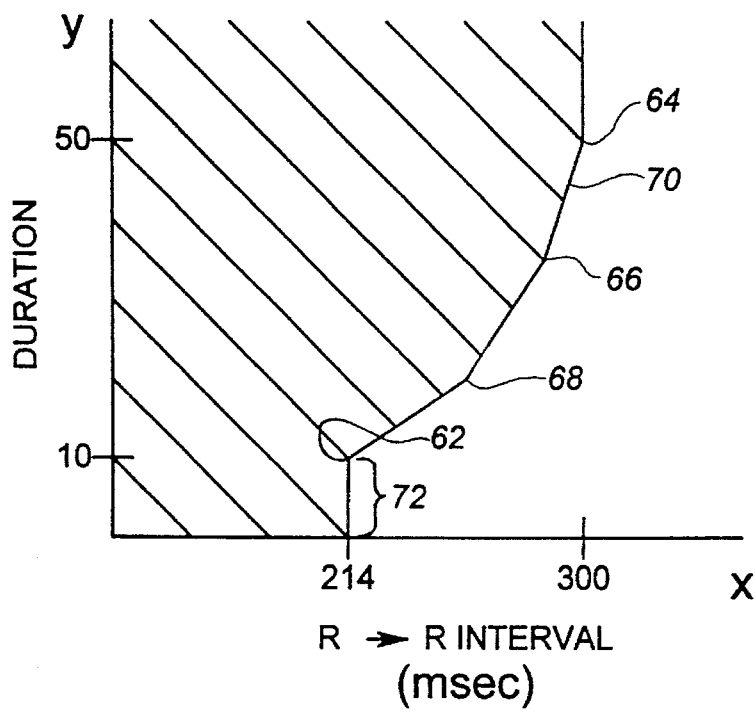
FIG. 8 is a graphic representation of a performance envelope defined by interdependent detection parameter settings between instability and R to R interval detected further defining a rate ruling zone.

FIG. 7 is a graphic representation of a detection envelope using the relationship between duration and R to R interval. The cardiac cycle, as depicted by an electrocardiogram in common use, describes an electrical curve. To those skilled in the art, the ventricular contraction portion represented in the EKG curve is known as the QRS pattern. The R portion or R-wave of the QRS is the first upgoing deflection. Each ventricular contraction has an associated QRS wave in the EKG. The ventricular rate is inversely proportional to the R to R interval. The R to R interval is given in milliseconds. As shown in FIG. 7, boundary condition curve 60 is defined by placement of corner points 62, 64, 66 and 68. FIGS. 7 and 8 are illustrative of the use of more than two corner points in defining a boundary curve. This invention makes use of the practicality and advantages of using a plurality of, e.g. up to about ten, corner points to increase the invention's accuracy in diagnosing cardiac dysrhythmias. For FIG. 7, corner points 62, 64, 66 and 68 have been chosen to be a representative example in the determination for the presence or absence of ventricular fibrillation. Each corner point chosen represents an interdependent detection parameter threshold. In FIG. 7, any point determined to fall within the hash mark area will be considered by the present invention to represent the diagnosis of ventricular fibrillation.

FIG. 8 depicts a graphic representation of a boundary condition curve 70 similar to curve 60 of FIG. 7. For ease of discussion, curve 70 of FIG. 8 is defined by the same four corner points 62, 64, 66 and 68 with the additional modification provided by a rate ruling zone 72 which has the same operative characteristics as rate ruling zone 48 of FIG. 4 and rate ruling zone 58 of FIG. 6.

Figure 9:
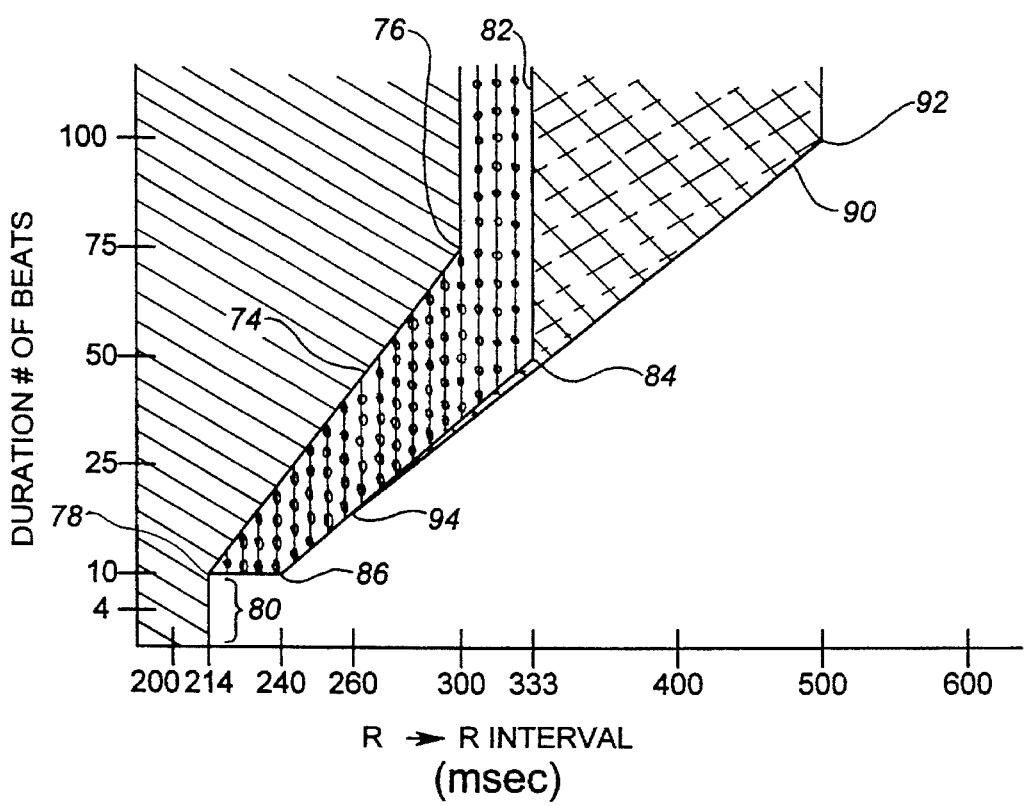
FIG. 9 is a graphic representation of the invention using a plurality of interdependent detection parameter thresholds defining a multiplicity of detection envelopes using duration versus R to R interval and allowing for rate ruling zones.

FIG. 9 is a graphic representation of the present invention monitoring duration versus R to R interval as the detection parameters. In FIG. 9, the present invention has been configured to demonstrate detection of ventricular fibrillation, high rate ventricular tachycardia, low rate ventricular tachycardia, and to delineate these dysrhythmias from each other. A ventricular fibrillation detection envelope is defined by boundary condition curve 74 chosen by plotting interdependent detection parameter thresholds at corner points 76 and 78. Additionally, for ventricular fibrillation a rate ruling zone 80 is also defined. Any detected parameter falling within the diagonal hash mark area defined by curve 74 will result in a diagnosis of ventricular fibrillation and appropriate treatment will be instituted.

High rate ventricular tachycardia has been defined by boundary condition curve 82 by choosing interdependent detection parameter thresholds as corner points 84 and 86 to define the detection envelope bounded by curve 82. A rate ruling zone, in this example, has not been chosen for high rate ventricular tachycardia. Such a decision is left to the physician attending the patient. The physician's decision might be that any high rate ventricular tachycardia that has a duration less than ten is not sufficiently debilitating to warrant the exigency surrounding electrical countershock therapy.

Low rate ventricular tachycardia is defined by boundary condition curve 90 chosen by selecting interdependent detection parameter thresholds as corner points 92 and 94. In FIG. 9, corner point 94 has been chosen to fall on curve 80 demonstrating one characteristic of high rate versus low rate ventricular tachycardia in that they are difficult to distinguish at the higher rates. All three of the boundary condition curves 70, 80, and 90 can be changed by reprogramming different interdependent detection parameter threshold parameter corner points 72, 74, 82, 84, 92, and 94. The latitude in choosing at least two values for each curve independently provides unanticipated flexibility in defining detection envelopes controlling an ICD's response to detection of a ventricular dysrhythmia.

Figure 10:
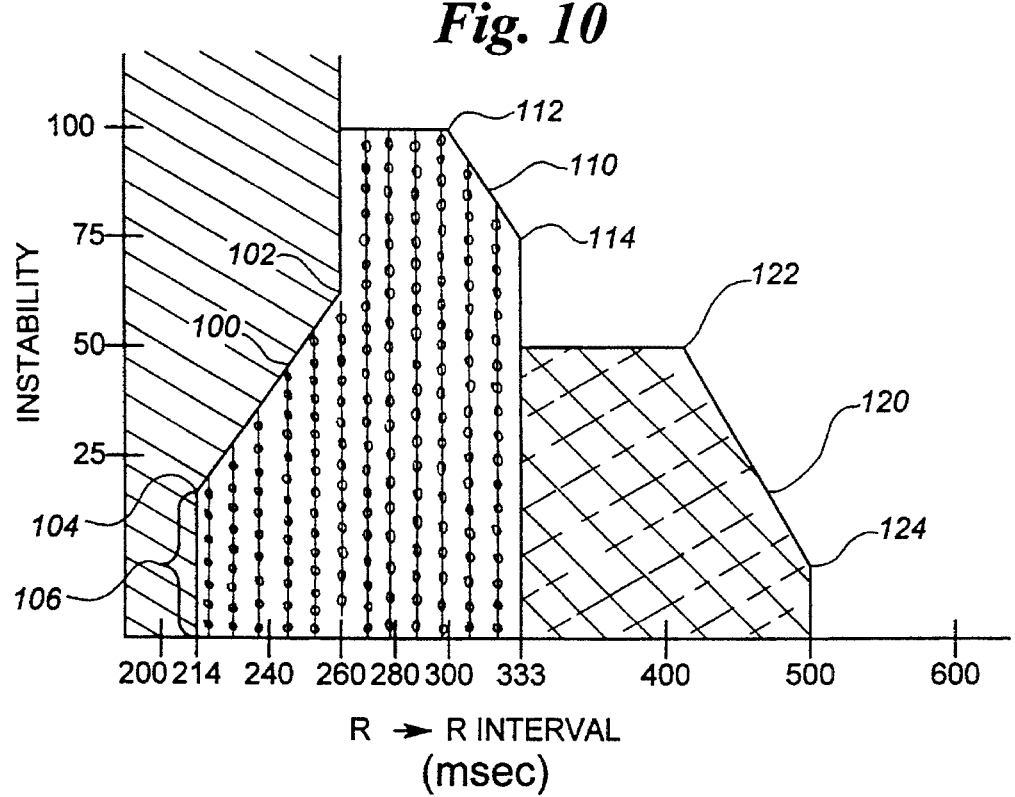
FIG. 10 is a graphic representation of the invention using a plurality of interdependent detection parameter thresholds defining a multiplicity of detection envelopes using instability versus R to R interval and allowing for rate ruling zones.

FIG. 10 is a graphic representation of the detection envelopes that might be generated using instability and R to R interval as the detection parameters. As shown in FIG. 10, ventricular fibrillation has been defined by boundary condition curve 100 by choosing corner points 102 and 104. Additionally, a rate ruling zone 106 has also been incorporated to allow a determination of ventricular fibrillation for any R to R interval shorter than 214 milliseconds. Curve 100 is a representative example of a useful curve recognizing that a physician in attendance may choose other points to generate a different curve based on the physician's judgment as to the needs of the individual patient. Such a consideration is true for generating high rate ventricular tachycardia detection envelope curves as well as low rate ventricular tachycardia detection curves. This flexibility is further demonstrated in FIG. 10 where high rate ventricular tachycardia is defined by boundary condition curve 110 by choosing corner points 112 and 114. As shown in FIG. 10, corner point 112 could represent a determination by a physician that high rate ventricular tachycardia in this R to R interval range has a degree of instability that is still consistent with characteristics of high rate ventricular tachycardia. Any shorter R to R interval at such high instabilities would put a determination into the ventricular fibrillation area. The line and circle hash area depicting high rate ventricular tachycardia further demonstrates the increasing stability characteristic of ventricular tachycardia as the area fills in towards corner point 104 and the rate ruling zone 106. Thus, the high rate ventricular tachycardia detection envelope conforms well to the expected characteristics of high rate ventricular tachycardia. A low rate ventricular tachycardia detection envelope has been defined by boundary condition curve 120 by choosing corner points 122 and 124 as interdependent detection parameter thresholds. The cross hatch area denotes the detection envelope area whereby any point detected by an ICD falling within the area would result in a diagnosis of low rate ventricular tachycardia. As boundary condition curve 120 demonstrates, the characteristic of low rate ventricular tachycardia is one of increasing stability and choosing a corner point 124 would demand that the ventricular dysrhythmia at R to R intervals of 500 milliseconds be extremely stable in order to warrant treatment by the present invention. Corner point 122 further controls the response by the present invention to R to R intervals of increasingly shortened duration by demanding that there be a reasonable degree of stability above which the system will not return a diagnosis of low rate ventricular tachycardia. This reasoning is consistent with the known physiologic effects of exercise and stress whereby R to R intervals will fall in the same general area between 333 milliseconds and 500 milliseconds but characteristically will have increasing instability as the R to R interval shortens. Stress related and exercise induced ventricular tachycardias do not warrant electrical countershock intervention by an ICD.

Figure 2:
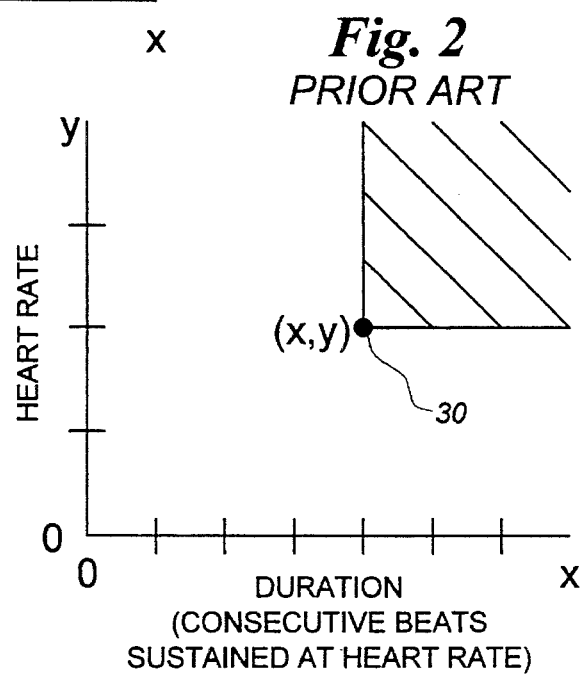
FIG. 2 is a graphic representation of a prior art use of heart rate and duration as detection parameters for the detection of a ventricular dysrhythmia.

The present invention allows a physician in attendance the flexibility of defining performance envelopes for at least three ventricular dysrhythmia subtypes, specifically ventricular fibrillation, high rate ventricular tachycardia and low rate ventricular tachycardia. Ease of selection is inherent in the physician only having to choose a minimum of two points to characterize each performance envelope. The unanticipated advantage realized by such a system is the increased ability to conform an ICD's response more appropriately to known physiologic characteristics of normal versus abnormal ventricular tachycardias and dysrhythmias. As was demonstrated in FIGS. 1 and 2, the logical combinational single point determinations severely limit those responses regardless of how many detection parameters can be programmed into that ICD. In the present invention, for example, by utilizing just duration instability heart rate and R to R interval demonstrates significant advancement in the approach and treatment to the various subtypes of ventricular tachycardia and dysrhythmia.

We claim:

1. A method for detecting and treating a plurality of cardiac dysrhythmias in an ailing human heart using an implantable programmable automatic cardioverter defibrillator electrically connected to a plurality of implantable electrodes placed proximate the human heart, the method comprising the device-implanted steps of:

a) providing a plurality of cardiac sensing modalites;

b) selecting from the plurality of sensing modalites a set of two or more corner point values for each sensing modality provided;

c) programming at least two sets of corner point values into the cardioverter defibrillator;

d) combining the selected sets of corner point values within the programming as interdependent detection parameter thresholds defining a plurality of cardioverter defibrillator detection envelopes;

e) detecting a cardiac dysrhythmia falling within the detection envelopes;

f) diagnosing a cardiac dysrhythmia from results of the detected cardiac dysrhythmia based on the detection envelopes; and g) providing a cardioverter defibrillator treatment regimen consistent with the diagnosed cardiac dysrhythmia.

2. The method of claim 1 in which the step of providing a plurality of cardiac sensing modalities comprises providing a range of modalities selected from a list of modalities consisting of: cardiac electrical cycle rates; ventricular beat to beat intervals; ventricular interval instability; duration periods during which cardiac cycle rates are measured; and acceleration of cardiac electrical cycle rates.

3. The method of claim 1 in which step d defines at least three combined detection envelopes, one each for ventricular fibrillation, high rate ventricular tachycardia and low rate ventricular tachycardia.

4. The method of claim 1 further comprising the step of modifying at least one of the selected sets of corner point values to include a rate ruling zone.

5. A cardiac dysrhythmia detection system for a programmable implantable cardioverter defibrillator that determines whether one or more preprogrammed electrical countershock therapies should be delivered through a plurality of implantable electrodes placed proximate a human heart, the detection system comprising:

means for providing electrical signals representative of a plurality of cardiac sensing modalities; and control means for analyzing the electrical signals and, in response, determining whether a preprogrammed electrical countershock therapy should be delivered by the implantable cardioverter defibrillator, the control means including:

memory means for storing values defining one or more interdependent detection parameter thresholds, each threshold being established for a programmably selectable combination of two or more of the plurality of cardiac sensing modalities by selecting at least two corner points as a set of corner points that define a boundary condition for the particular combination of the plurality of cardiac sensing modalities for a given cardiac dysrhythmia;

means for comparing the electrical signals to the one or more interdependent detection parameter thresholds and automatically diagnosing a cardiac dysrhythmia whenever the interdependent detection parameter thresholds are exceeded by the electrical signals for the particular combination of cardiac sensing modalities; and means for selecting one or move preprogrammed electrical countershock therapies to be delivered in response to the means for comparing.

6. The detection system of claim 5 in which the means for comparing uses combination of two or more cardiac sensing modalities to define a multivariant boundary condition for the given cardiac dysrhythmia.

7. The detection system of claim 5 in which the plurality of cardiac sensing modalities comprises providing a range of modalities selected from a list of modalities consisting of: cardiac electrical cycle rates; ventricular beat to beat intervals; ventricular interval instability; duration periods during which cardiac cycle rates are measured; and acceleration of cardiac electrical cycle rates.

8. The detection system of claim 5 in which the memory means defines more than one set of corner points for a particular combination of cardiac sensing modalities so as to create a detection envelope for each of a different type of cardiac dysrhythmia.

9. The detection system of claim 8 in which the memory means uses more than one set of corner points for a particular combination of cardiac sensing modalities to define at least three combined performance envelopes, one each for ventricular fibrillation, high rate ventricular tachycardia and low rate ventricular tachycardia.

10. The detection system of claim 5 further comprising means for modifying at least one or more interdependent detection parameter thresholds to include a rate ruling zone.

* * * * *